(12) United States Patent
Ifejika

(10) Patent No.: US 6,363,953 B1
(45) Date of Patent: Apr. 2, 2002

(54) DEVICE FOR CLEANING CONTACT LENS AND SIMILAR UTILITY ITEMS

(76) Inventor: Charles Philips Ifejika, Flat 3, 55 Iverson Road, London NW6 2QT (GB)

( * ) Notice: Subject to any disclaimer, the term of this patent is extended or adjusted under 35 U.S.C. 154(b) by 0 days.

(21) Appl. No.: 09/403,738
(22) PCT Filed: Apr. 28, 1998
(86) PCT No.: PCT/GB98/01235
§ 371 Date: Jan. 18, 2000
§ 102(e) Date: Jan. 18, 2000
(87) PCT Pub. No.: WO98/49595
PCT Pub. Date: Nov. 5, 1998

(30) Foreign Application Priority Data

Apr. 29, 1997 (GB) .............................................. 9708647

(51) Int. Cl.[7] .................................................. B08B 3/04
(52) U.S. Cl. ...................... 134/140; 134/146; 134/155; 134/158; 134/162; 134/901
(58) Field of Search ................................ 134/901, 95.1, 134/140, 146, 155, 157, 158, 162

(56) References Cited

U.S. PATENT DOCUMENTS

| | | | |
|---|---|---|---|
| 4,776,360 A | * 10/1988 | Ching Shih | 134/901 X |
| 4,852,592 A | * 8/1989 | DiGangi et al. | 134/901 X |
| 5,161,559 A | * 11/1992 | Yoshihara et al. | 134/901 X |
| 5,456,276 A | * 10/1995 | Shun-Hsien | 134/901 X |

FOREIGN PATENT DOCUMENTS

| | | |
|---|---|---|
| WO | WO-89/00429 A | * 1/1989 |
| WO | WO-94/22498 A | * 10/1994 |

* cited by examiner

*Primary Examiner*—Philip Coe
(74) *Attorney, Agent, or Firm*—Theresa Fritz Camoriano; Camoriano and Associates

(57) ABSTRACT

A device for cleaning contact lenses, which device comprises a first chamber (1) provided with draining means (3,8), a second chamber (2) adapted to be fluidly communicable with the first chamber (1), a lens holder (20) adapted to be inserted in the first chamber (1) and agitating means (22–28) adapted to agitate the lens holder, wherein the device further comprises a valve (5) adapted to control fluid flow between the first chamber (1) and the draining means (3,8) and between the first (1) and second chambers (2). The valve (5) can be automatically controlled.

11 Claims, 2 Drawing Sheets

DEVICE FOR CLEANING CONTACT LENS AND SIMILAR UTILITY ITEMS

The present invention relates to a device for cleaning utility items, such as electrical components, medical and scientific equipment and in particular, but not exclusively contact lenses.

Many utility items, especially from the medical field, require thorough cleaning and sometimes sterilisation. In particular it is often preferable that microbial contamination from all sources is minimized. In particular, microbial contamination is a significant problem with contact lenses.

Infections due to microbial keratitis, acanthamoeba or ulcerative keratitis are recurring problems associated with contact lens wear. The problems may arise for example when a contact lens is not cleansed sufficiently by the lens wearer, and the bacterial load of the lens increases such that a biofilm forms on the lens. In such cases not all lens cleaning solutions may be strong enough to kill residual bacteria. Similarly the contact lens may harbour infectious organisms such as acanthamoeba, which can also contaminate the lens case in addition to the lens resulting in time in a devastating keratitis.

A problem facing the lens wearer is that known lens care systems do not provide for ease of use. Typically lens wearers are required to clean their lenses for 10–30 seconds with their fingers using a cleaning solution before rinsing the lens and disinfecting the lens, which may take up to six hours. Often the lens has to be rinsed again prior to insertion. It is well known that many lens wearers omit one or more of these steps resulting in lens wear complications, frequently leading to infection. More convenient lens solutions have been proposed but as with the other known solutions, if the instruction are not followed carefully, the rate of lens wear complication may increase.

Another well known problem is that sometimes during lens wear, the eye may feel dry or the lens uncomfortable. Also occasionally lenses fall out. In such cases, the lens should be cleaned before re-insertion.

Various devices have been proposed which assist with either cleaning or sterilising, but no devices have been marketed which are convenient to use and remove the user from responsibility for cleaning and sterilising.

One such apparatus is disclosed in EP 0394254, which discloses apparatus comprising an agitator with a reciprocating motion, which apparatus is adapted to clean the lens in a short time with minimal effort.

The problem underlying the invention is therefore to provide a device which enables contact lens wearers to clean and disinfect their lenses in a single process with little or no effort or maintenance on their part.

According to the invention the problem is solved by a device made as described herein.

The device of the invention has the advantage over the known devices that it permits a very thorough and efficient cleaning of lens without the risk of contamination. Moreover the device is also very compact and portable in comparison with other known devices due to the reduction in the number of components required to obtain a satisfactory cleaning operation, in particular by using a 2/2 or 3/2 valve in place of the known multivalve arrangements.

Preferably, the valve is provided with control means so that each stage of the procedure may be carried out without intervention from the wearer. This advantageously requires only a single actuation by the user and therefore is very convenient to use.

An exemplary embodiment of the invention will now be described in which.

Figure 1A:
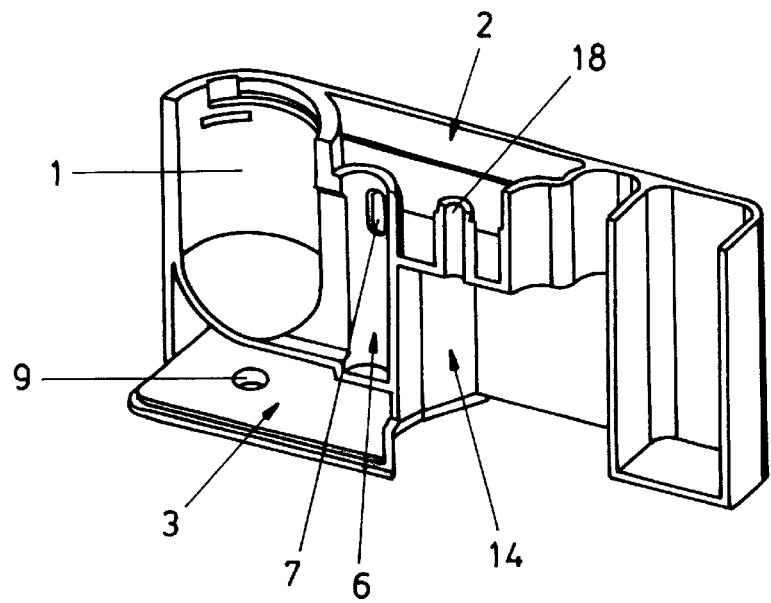
FIG. 1a shows a perspective cross-sectional view of the device housing.
Figure 1B:
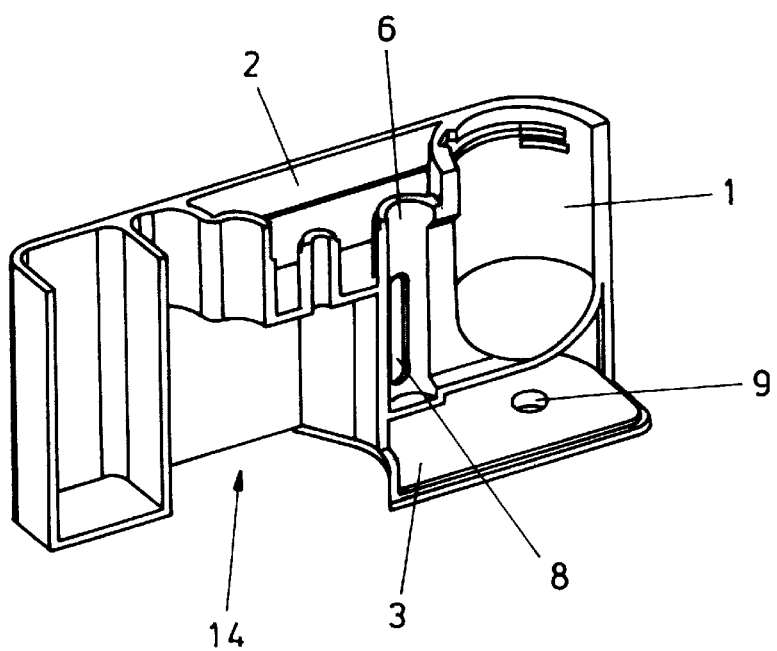
FIG. 1b shows a perspective cross-sectional view from the opposition direction.
Figure 1C:
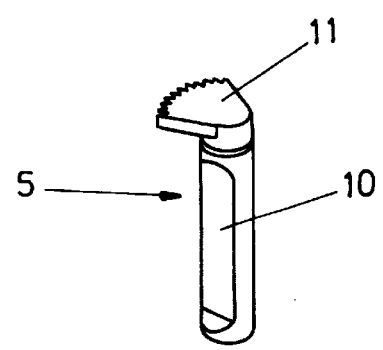
FIG. 1c shows a valve body.

The housing of the device comprises a first chamber 1 adapted to receive a contact lens holder, a second chamber 2 and a drain chamber 3. The second chamber acts to refill the first chamber and is therefore located adjacent to and at an upper level of the first chamber. The drain chamber is located below the first chamber. A valve housing 6 having a substantially circular wall, which is located between the first chamber 1 and the second chamber 2 and the first chamber 1 and the drain chamber 3, is provided with a first slot 7 in its wall to provide for fluid communication between the first and second chambers and a second slot 8 in its wall opposing the first slot 7 to provide for fluid communication between the first 1 and drain 3 chambers. The second chamber can thus act as a reservoir for the first chamber 1. The drain chamber 3 is provided with an exit hole 9 having a plug.

Adjacent to the first, second and drain chambers, the device housing comprises a compartment 14 adapted to receive a motor, control electronics and switch together with a power supply such as batteries. An opening is provided at an upper surface of this compartment leading to a bore 18 which extends through and is isolated from the second chamber. The bore 18 is adapted to receive a drive shaft from the motor.

The valve body 5 has a substantially cylindrical body, which body is adapted to form a fluid seal in the valve housing, having a segment 10 removed from one portion of its surface, which segment is tapered at its upper and lower ends to assist with fluid flow in use.

Rigidly connected to the upper end of the valve body is a ratchet 11 corresponding substantially to a sector of a gear wheel, which ratchet is a part of a clutch mechanism in use.

Figure 2:
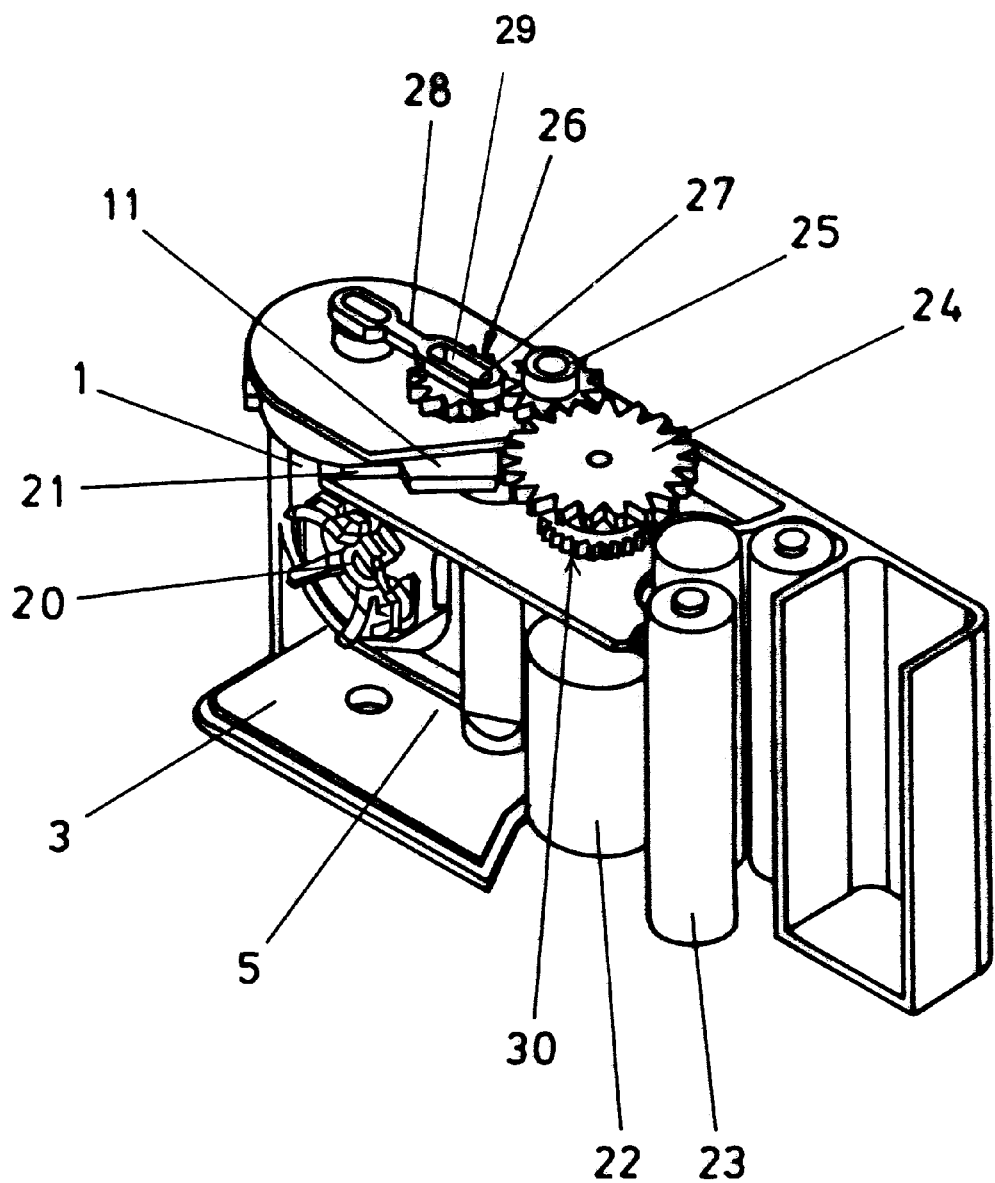
FIG. 2 shows a perspective cross-sectional view of the assembled device.

FIG. 2 shows the assembled device without lid feature in which a lens holder 20 supported on a rod 21 is positioned in the first chamber 1. The lens holder 20 comprises a support adapted to allow fluid flow around each of a pair of lenses. The valve 5 is inserted in the valve housing 6. A motor 22 having a driveshaft is located in the compartment 14. The power for the motor 22 is provided by three conventional dry batteries 23.

A gear wheel 24 is located at the end of the driveshaft remote from the motor, which gear wheel meshes via a smaller idler gear wheel 25 with a further gear wheel 26 provided with an off centre pivot 27. The gear wheel 26 is drivingly coupled to the rod 21 by a further rod 28 having a slot 29 for the off centre pivot 27. The gear train, in use, provides the agitation for cleaning the lenses.

A further gear wheel 30 is mounted on the driveshaft intermediate to the gear wheel 24 and the motor 22, which gear wheel 30 forms part of the clutch mechanism for driving the valve 5.

The ratchet 11 is biased against a stop by a spring. When the driveshaft is driven in a first direction, the gear wheel 30 does not drivingly engage the ratchet as this is in its rest position. This may be achieved by providing the gear wheel 30 with sufficient slip on its bearings that it does not jam the mechanism or alternatively by providing some resilience in the stop position.

When the driveshaft is driven in the opposite direction to the first direction, the gear wheel 30 drivingly engages the ratchet 11 and turns this about its axis to its opposite extremity subject to the return spring force. As the ratchet 11 is rigidly connected to the valve body 5, this is then turned in its housing between its respective first and subsequent positions.

Due to the spring force, when the drive shaft resumes its original direction, the ratchet 11 will be returned by the gear wheel 30 to its initial position.

It can thus be seen that the ratchet 11 and the gear wheel 30 form part of a clutch mechanism. Alternatively to the toothed wheel type connection, it would be equally possible to use other clutch type coupling such as a frictional connection.

The first chamber 1 may be filled from the top and is sealingly closed by a cap integrated with the rod supporting the lens holder. The second chamber may be filled either via its own access hole or via the first chamber if the valve is a 2/2 valve. The gear mechanism is preferably provided with a closing cap which mates with the cap of the first chamber to seal the unit.

The motion of the clutch mechanism and hence of the valve body 5 is controlled via a control device comprising simple electronic circuitry. Although, the valve body is preferably controlled automatically to reduce wearer input on the cleaning process, it would be possible to actuate the valve body manually. In a first embodiment where the valve is a 2/2 valve, the first and second chambers are filled with the same cleaning solution, the control device actuates the motor to rotate in a first direction, causing the lens holder to be agitated, for a predetermined period of time, typically 60 seconds. In the initial position the valve is open between the first chamber and the second chamber.

After 60 seconds, the direction of rotation of the driveshaft is changed and the valve body is rotated and closes the passage between the first and second chambers and subsequently the passage between the first and drain chambers is opened. The direction is changed for a predetermined time sufficient to ensure that the contents of the first chamber can drain into the drain chamber. This period is typically ten seconds.

Then, the first direction is resumed and the drain passage is closed and the passage between the first and second chambers is re-opened so that the first chamber may be refilled. The lens holder is then agitated for a further predetermined period, typically 60 seconds. Thereafter the lenses may be removed.

In an alternative embodiment the valve is a 3/2 valve. In this embodiment, in the initial position the valve closes off the passages between the first chamber and the second chamber and between the first chamber and the drain chamber. The contact lens chamber is agitated as before, then upon reversal of the motor, the drain passage is opened, draining the liquid and then this is closed and the passage between the first and second chambers is opened. In this case, the motor runs in the reverse direction for a longer predetermined period of time, say 60 seconds. At the end of the period the valve can be reset to its initial position. This alternative embodiment enables the first and second chambers to be filled with different solutions.

In each of the embodiments described above it is possible to reverse the direction of the driveshaft for a further period of time prior to switching off the motor so that the contents of the first chamber can drain into the draining chamber.

The design of the valve and drain chamber could be so arranged that the valve or fluid controller does not reverse but moves periodically or sequentially in a 360° motion. The apparatus could comprise two equally upwardly housed filling chambers, each holding separate solutions which would enable more than one cleaning and rinsing procedure to take place. One of these filling chambers could be adapted to be filled separately to enable the apparatus to receive two fluids that must not interact with each other until a predetermined time.

The reversible embodiment of the invention could be reversed by means of small protruding component parts situated upon the top of the ratchet 11 and on the underside of the gearwheel 24. As the gearwheel is sequentially reversed, the protruding parts gently collide and thereby move the ratchet 11 into the appropriate position for draining or refilling. So long as there is means to automatically control the direction and/or motion of the valve or fluid controller, which works in concert with the agitating means to provide thorough cleaning of utility items, preferably requiring only a single actuation by the user.

The valve housing and valve body may be made of a suitable plastics material, provided that a sufficient seal between the housing wall and the valve body wall is obtained.

The agitation means described above provides the lens holder with agitation, such motion having preferably both a vibratory and a reciprocating component. Such a combination of motions has been found to be particularly effective in reducing bacterial counts at frequencies of above about 45 Hz. The embodiment described has the advantage that it is a particularly compact and portable solution. It would however be quite feasible to provide alterative mechanisms capable of producing such motion, e.g. eccentric and push-rod.

Although in the invention as described above a single motor is used to drive both the valve and the agitation motion, it would be possible to use separate drive means for each. Also alternative power sources, e.g. clockwork, could be used. Although the invention as described relates to cleaning contact lenses, it could also be used for cleaning other items such as small electrical components or scientific equipment.

What is claimed is:

1. A device for cleaning contact lenses, which device comprises a first chamber (1), a second chamber (2), a lens holder (20) adapted to be inserted in said first chamber (1), wherein the first chamber (1) is provided with draining means (3,8) and the second chamber is adapted to be fluidly communicable with the first chamber, and the device further comprises a valve (5) adapted to control fluid flow between said first chamber (1) and said draining means (3,8) and between said first (1) and second chambers (2) characterised in that the device further comprises agitating means (22–28) adapted to agitate said lens holder (20) and valve control means (11,22,30), including a power source (22), which is adapted to be drivingly connected to the valve (5) such that the valve body is movable between respective first and second positions, the power source being coupled to the agitating means.

2. A device according to claim 1, characterised in that the device comprises means for motion control which is drivingly connected to the valve and is additionally adapted to agitate the lens holder at the same time.

3. A device according to claim 1, characterised in that the power source is a motor (22), which motor is adapted to agitate the lens holder (20) and move the valve (5) in a first direction, and thereafter agitates the lens holder (20) and moves the valve in a second, opposite, direction.

4. A device according to claim 3, characterised in that the motor rotates in a first direction to agitate the lens holder (20), said motor being adapted to rotate the valve body (5) in a second direction.

5. A device according to claim 4, characterised in that the control device is adapted to drive the motor (22) in a first direction for a predetermined period of time, the control device then actuates the valve (5) to close the connection between the first and second chambers (1,2), and then open the connection between the first chamber (1) and the draining means (3) for a predetermined period of time.

6. A device according to claim 4, characterised in that the connection between the draining means (3) and the first chamber (1) is closed and the agitating means is actuated for a second predetermined period of time after the connection between the first chamber and second chamber (2) has been re-opened.

7. A device according to claim 3, characterised in that the motor is drivingly connected via a clutch mechanism having first and second clutch parts (11,30) to the valve (5), such that the valve body is rotatable between the first and second positions.

8. A device according to claim 7, characterised in that the first clutch part (30) is a gear wheel and the second clutch part is a ratchet (11), said gear wheel meshing with the ratchet, which ratchet is coupled to the valve (5).

9. A device according to claim 7, characterised in that the device comprises first stop means adapted to retain the first and second clutch parts (11,30) drivingly coupled to one another in said first direction and means adapted to bias the second clutch part in its initial position, whereby the valve (5) is actuated when the second clutch part is moved from its initial position.

10. A device according to claim 7, characterised in that the agitating means is drivingly connected to the motor (22) by a gear train (24,25,27), wherein the lens holder (20) is coupled to the final gear (26) via a rod (28) with a slot, which engages with an off centre pivot (27) on said final gear thereby providing agitation.

11. A device according to claim 1, characterised in that the valve (11) comprises a substantially cylindrical valve body in a housing (6), said body having a segment (10) removed from a central portion to provide a flow opening, wherein the valve control means is adapted to rotate said body in said housing between the respective positions of the valve.

* * * * *